(12) United States Patent
Kenney

(10) Patent No.: US 6,551,849 B1
(45) Date of Patent: Apr. 22, 2003

(54) METHOD FOR FABRICATING ARRAYS OF MICRO-NEEDLES

(76) Inventor: Christopher J. Kenney, 2329 Sharon Rd., Menlo Park, CA (US) 94025

(*) Notice: Subject to any disclaimer, the term of this patent is extended or adjusted under 35 U.S.C. 154(b) by 201 days.

(21) Appl. No.: 09/705,460

(22) Filed: Nov. 2, 2000

Related U.S. Application Data

(60) Provisional application No. 60/163,140, filed on Nov. 2, 1999.

(51) Int. Cl.⁷ .............................................. H01L 21/00
(52) U.S. Cl. ......................................... 438/34; 438/42
(58) Field of Search ...................... 438/34, 42

(56) References Cited

U.S. PATENT DOCUMENTS

| | | |
|---|---|---|
| 5,855,801 A | 1/1999 | Lin et al. |
| 6,033,928 A | 3/2000 | Eriguchi et al. |
| 6,087,197 A | 7/2000 | Eriguchi et al. |
| 6,132,278 A * | 10/2000 | Kang et al. .............. 445/14 |
| 6,393,685 B1 * | 5/2002 | Collins ..................... 29/416 |

* cited by examiner

*Primary Examiner*—John F. Niebling
*Assistant Examiner*—Lynne A. Gurley

(57) ABSTRACT

An array of micro-needles is created by forming an array pattern on the upper surface of a silicon wafer and etching through openings in the pattern to define micro-needle sized cavities having a desired depth. The mold thus formed may be filled with electrically conductive material, after which a desired fraction of the silicon wafer bulk is removed from the bottom-up by etching, to expose an array of projecting micro-needles. The mold may instead be filled with a flexible material to form a substrate useful in gene cell probing. An array of hollow micro-needles may be formed by coating the lower wafer surface with SiN, and etching through pattern openings in the upper surface down to the SiN layer, and then conformally coating the upper surface with thermal silicon dioxide. The SiN layer is then stripped away and a desired fraction of the bulk of the wafer removed from the bottom-up to expose an array of projecting hollow micro-needles.

16 Claims, 12 Drawing Sheets

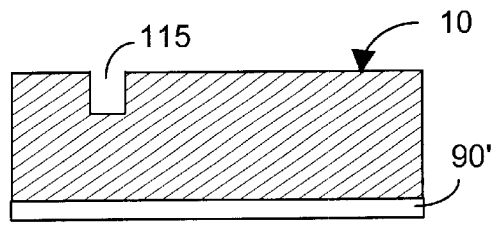
FIG. 1O
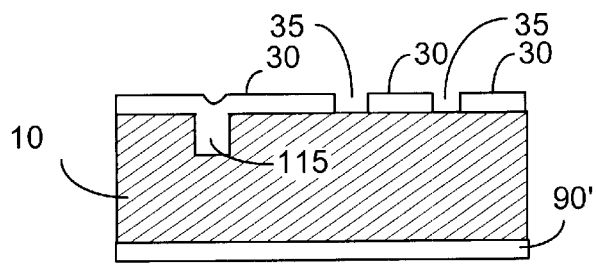
FIG. 1P
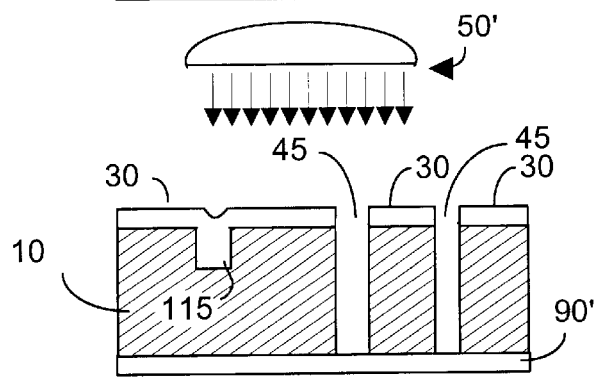
FIG. 1Q
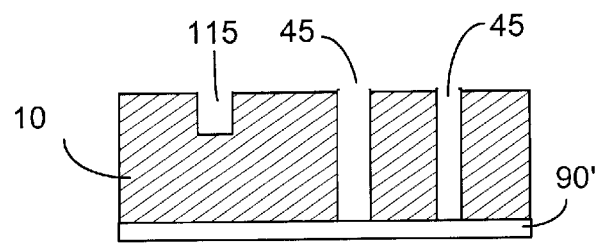
FIG. 1R
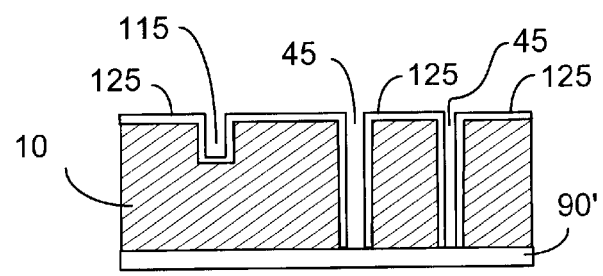
FIG. 1S
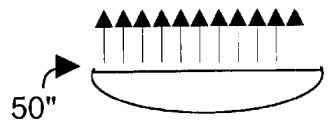

METHOD FOR FABRICATING ARRAYS OF MICRO-NEEDLES

RELATIONSHIP TO PENDING APPLICATIONS

Priority is claimed from U.S. provisional patent application serial No. 60/163,140 filed on Nov. 2, 1999, and entitled "Method for Fabricating Arrays of Micro-Needles", in which Christopher J. Kenney is inventor and in which University of Hawaii is assignee.

GRANT PATENT RIGHTS

Portions of the underlying research were funded by the U.S. Dept. of Energy, grant DEFG0394ER40833, via the University of Hawaii. The U.S. Dept. of Energy may have rights in this patent application.

FIELD OF THE INVENTION

The invention relates generally to micro-sized devices that can be used to manipulate very small quantities of gases or liquids, or as conductive probes or neural stimulators, or to provide a plurality of test surfaces for gene probes, and more specifically to methods for fabricating arrays of such micro-sized structures.

BACKGROUND OF THE INVENTION

In scientific fields such as micro-fluidics and combinatorial chemistry it is often necessary to manipulate very small quantities of gases or liquids is required, for example volumes as small as a picoliter or so. Understandably it is difficult to fabricate hollow micro-needles dimensioned for such tasks, especially where needle lengths exceeding 1 mm are required. Without limitation, such micro-needles can or should find application in the dispensing and manipulation of DNA samples, in fabricating so-called gene IC chips for example.

Conventional DNA sampling is often carried out using an array of perhaps forty-eight needles, a relatively low number. The needles in the array are typically rigid, made of stainless steel, and are rather expensive. Various of the needles are exposed to a solution that may contain DNA or other biological or chemical materials, and the needle tips are then urged against regions on a substrate. Substrate regions may be coated with various DNA, biological, or other chemical samples, with which the materials transported via the needles may react. A very real problem is avoiding fracturing the needles as they meet the typically rigid glass substrate, and avoiding cross-contamination between various sample solutions. Often the needles are individually spring loaded, and the relatively non-dense arrays help guard against cross-contamination. But it would be desirable to use probe arrays containing thousands or tens of thousands or more of individual needle-probes. It would be highly useful to be able to provide a substrate useable with such dense arrays of needle probes, or indeed useful with existing rigid low density probes, which substrate would be somewhat flexible and would define different test regions.

In a standard gene chip or gene cell procedure, the chips are patterned with an array of spots of distinct DNA samples. The chip is then exposed, for example by soaking in a solution containing cDNA samples taken from a piece of tissue, a tumor perhaps. More specifically, RNA is taken from the tissue and converted into corresponding DNA, which is then replicated via PCR. Thus in standard gene chips, when the needles deposit their samples the chip will be bare or empty. But in combinatorial chemistry, or in material science applications, samples may already be present.

In other fields, small preferably solid micro-needles are desired as probes to sense electrical signals, or as probes to apply stimulation electrical signals, such as from neural tissue or other complex media. Without limitation, suitably sized hollow and/or solid micro-needles could find application in neural stimulation, sensing, sampling, injection, light absorbing sensors, and light emitting surfaces. Other applications should include micro-scale or nano-scale "stamps" such as so-called cookie-cutter tools used in micro-scale or nano-scale applications. Appropriate micro-needles should also find application as electron emitters, for example in high electric field avalanche multiplier structures. Appropriate micro-needles should also find use in gaseous-based or liquid-based detectors of ionizing radiation. Appropriate hollow micro-needles may also be used as extrusion nozzles in micro-sale or nano-scale applications.

Thus there is a need for a method to produce micro-needles, and arrays of such micro-needles, that may be hollow or solid in cross-section, and that preferably are electrically conductive, yet can be fabricated to be electrically isolated from each other. The method should produce micro-needles with diameters that can range from a few nanometers to several millimeters, with height/diameter aspect ratios ranging from under unity to more than one thousand. In cross-section, the resultant mold or micro-needle structures may have any configuration, including circular, rectangular, triangular, line segment, filled-in polygons, hollow polygons, etc. Depending upon materials used, e.g., thermal oxide, tungsten, etc., the resultant structures should function at temperatures exceeding 1,000° C.

Further, there is a need for a method to produce preferably flexible substrates that can define a dense array of individual surfaces suitable for micro-needle probing in a gene chip application. The flexibility of such substrates would minimize needle probe breaking and the individual surfaces formed on the substrate would minimize cross-contamination of samples.

Preferably a method of producing such structures should use techniques and equipment presently available for fabrication in the semiconductor industry. Once fabricated, such micro-needles, arrays, and substrates should find use in any or all of the various applications noted above.

The present invention provides such fabrication method for producing such micro-sized structures and arrays of such structures.

SUMMARY OF THE INVENTION

Solid and hollow micro-needle structures and arrays of such structures are fabricated by forming an electrical insulating layer on a standard silicon wafer. At least one wafer surface is polished, and is array-patterned. Material is then etched away from the bulk of the wafer through the pattern to form cavities where micro-needles are desired to be formed. The etch depth extends into the wafer a length corresponding generally to a desired length of the micro-needles to be formed. The etching forms a plurality of cavities extending from the wafer top into the bulk of the wafer. The cavities may taper inward or outward, be cylindrical or indeed have an hourglass or other shape, depending upon the techniques used to remove material from the wafer bulk.

The cavity cross-section dimensions may range from a few nanometers to several millimeters, and the height/ diameter aspect ratios may range from less than one to greater than one thousand. Pitch density may range from about 1 µm to about 1 cm. In cross-section, the mold cavities may have any desired configuration including circular, rectangular, triangular, line segment, filled-in polygons, hollow polygons, etc. Different mold cavities within an array may have different dimensions and shapes, if desired. Cavity depth may range from about 1 µm to the thickness of the wafer, perhaps 1 cm or so.

A sacrificial layer of polysilicon may now be deposited into the newly etched holes. The profile of what will be micro-needles is substantially vertical except near the distal tip, and such use of polysilicon can substantially increase the final height/diameter aspect ratio of the finished micro-needles.

At this juncture, the substrate may be used as a mold, in that the substrate defines an array of cavities extending into the substrate bulk. If electrically conductive micro-needles are to be formed, the cavities may be filled with an electrically conductive material, e.g., gold, tungsten, copper, nickel, perhaps aluminum, doped polysilicon. If it is desired to produce non-conductive micro-needles, the cavities may be filled with a non-conductive material, e.g., glass. In either case, substrate bulk material is then removed from the bottom of the wafer upwards to expose a desired length of the now conductive material filled micro-needles. If desired, electrically conductive contact pad, traces and wire bond pads may be fabricated to couple electrical signals to individual ones of the micro-needles in the resultant array. The micro-needles adopt the size and shape of the cavities formed in the mold.

If desired, the mold formed in the wafer bulk may be used to form a flexible substrate for DNA gene cell applications, in which individual elevated substrate regions or plateaus are defined by the cavities in the substrate. Cavity depth would determine plateau height, which is to say well depth if the structure is inverted, and patterning would determine array density and the cross-sectional configuration of various plateaus. The cavities formed in the substrate would be filled with an appropriate flexible material, for example, polydimethyl siloxane (PDMS). The substrate bulk would then be removed such that what is left is a honeycomb-like array of wells that preferably include concave regions separated from other wells by elevated perimeter walls projecting upward from the PDMS surface. Such PDMS material is flexible and would not break or deform DNA probes, and when used with micro-probes according to the present invention could provide array densities of tens of thousands of micro-needle probes that contact individual plateau regions on a flexible membrane substrate, also formed according to the present invention. Further, the present invention provides a method to produce cantilevered high density probes, suitable for contacting test pads and the like on integrated circuits.

Hollow micro-needles may be fabricated as well as solid micro-needles. However at the starting phase, the lower surface of the wafer is coated with silicon nitride (SiN) or the like. Etching through the patterned upper surface is continued through the wafer thickness, down to the upper regions of the SiN layer at the wafer bottom. Dimensions and configurations of the cavities may be as described above. Thermal oxide is then grown to cover all of the wafer including the sidewalls of the cavities formed, except of course for the SiN covered bottom region of the cavities. The SiN is then etched or otherwise removed, and substrate bulk material is removed from the bottom-up to expose a desired length of hollow glass micro-needles. If desired, the micro-needles could be coated to be electrically conductive, to present an array of hollow conductive micro-needles. Such micro-needles could be combined with micro-fluid pumps, fluidic channels, reservoirs, etc., for use in various applications.

Transistors and integrated circuits may be formed on the same wafer as the array of micro-needles and/or micro-probes. In applications requiring micro-needle dispensed fluids, tiny fluid reservoirs and/or fluid carrying channels may also be formed on the wafer. Application of electrical potential between the wafer substrate and micro-needles can encourage the fluid to prefer the substrate to a micro-needle, thus promoting fluid flow.

Additional structure may be added to the micro-needle wafer structure to build more complex systems. For example, fabricating electrode sets on parallel surfaces and coupling electrical drive signals to the electrodes can result in the controlled vertical displacement of selected micro-needles. In other applications, fluid may be dispensed onto a substrate or slide using a micro-needle fabricated according to the present invention, and application of electrical potential can assist in promoting the desired flow.

Non-biologic and genetic research applications can include fabricating capillary micro-needles for use in colloid micro-thruster arrays, for space propulsion application. Such colloidal micro-thrusters may comprise a charged colloid drop or jet emitter, fabricated from a micro-needle as described herein, following by a stack of one or more extractor plates. The micro-needle is centered above an opening in the first extractor plate, which serves primarily as a high voltage structure that induces injection of colloidal drops or jets from the emitter. The second and subsequent plates may be used to increase velocity (and thus thrust) provided by the emitted colloid drops, or may be used to modify trajectory and/or direction of the emitted drops or jets. The ability to thus change drop or jet trajectory and/or direction provides a vectoring capability for a propulsion system. Applications for such systems are disclosed in Cappelli, M. and Pranajaya, F. "Colloid Propulsion Development For Use in Microsatellite Applications", research report, Stanford Univ., May 1999.

Other features and advantages of the invention will appear from the following description in which the preferred embodiments have been set forth in detail, in conjunction with the accompanying drawings.

BRIEF DESCRIPTION OF THE DRAWINGS

FIG. 1O depicts a preliminary stage of a wafer in which a channel or reservoir is formed, and in which through hollow micro-needles will be formed, with a layer of SiN on the bottom wafer surface, according to the present invention;

FIG. 1P depicts the wafer of FIG. 1 with the addition of patterned resist that will define regions in which hollow micro-needles will be formed, according to the present invention;

FIG. 1Q depicts the wafer of FIG. 1P subjected to an etching process resulting in micro-needle sized cavities extending the thickness of the wafer, according to the present invention;

FIG. 1R depicts the wafer of FIG. 1Q after removal of resist, showing a channel or reservoir and two micro-needle sized through cavities, according to the present invention;

FIG. 1S depicts the wafer of FIG. 1R after deposition of a layer of thermal silicon dioxide, and depicts the wafer subjected to an etch process to remove the SiN layer on the lower wafer surface, according to the present invention;

DETAILED DESCRIPTION OF THE PREFERRED EMBODIMENT

Figure 1A:
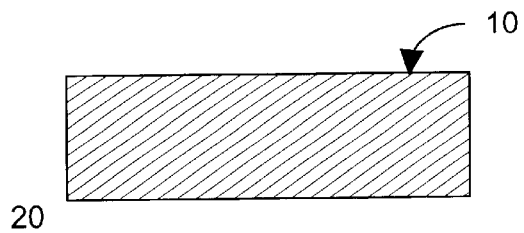
FIG. 1A depicts a standard silicon wafer, used to produce micro-needles according to the present invention.

FIG. 1A depicts a SEMI standard single crystal silicon wafer 10 that has been primed, polished on at least one side, and generally processed to conform to semiconductor standards. Wafer 10 may be used as a starting point for many of the fabrication methods described herein.

Assume that it is desired to fabricate upon wafer 10 an array of micro-needles, each needle being electrically isolated from the other needles in the array, and being individually electrically accessible, e.g., via a dedicated wire bond pad.

Figure 1B:
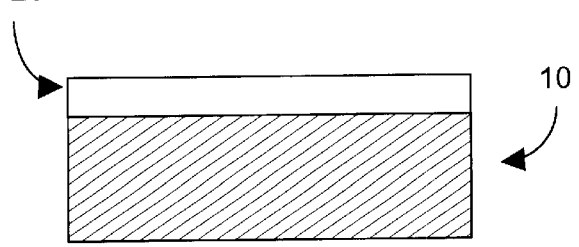
FIG. 1B depicts deposition of an insulator layer atop the wafer of FIG. 1A.

In FIG. 1B, wafer 10 has been covered with a deposition or grown of electrical insulator 20, which may be $SiO_2$, silicon nitride, among other materials. Thickness of layer 20 typically will be in the range of perhaps 1 $\mu$m to 2 $\mu$m.

The polished (here, upper) side of wafer 10 is spin coated with a layer of preferably thick photoresist 30, e.g., AZ4620 or Shipley SPR-220. The thickness of photoresist 30 is selected to be sufficient to withstand plasma etching, e.g., perhaps a thickness of 5 $\mu$m to 20 $\mu$m.

Figure 1C:
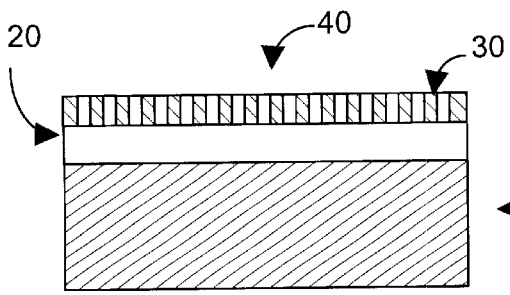
FIG. 1C depicts the wafer of FIG. 1B after a patterned layer of photoresist has been formed, according to the present invention.
Figure 2A:
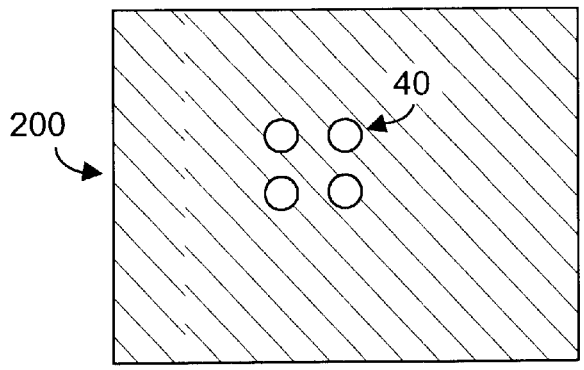
FIGS. 2A–2D depict exemplary masks used during formation of electrical traces and bonds for micro-needles, according to the present invention.

Referring briefly to mask 200 shown in FIG. 2A in which an exemplary hole pattern 40 is shown, and to FIG. 1C, photoresist 30 is exposed and patterned, preferably using commercially available alignment tools. The exposed photoresist 30 is developed, and any pre-bake or post-bake steps, as may be appropriate to the resist used, are carried out. Pattern 40 in photoresist 30, formed using mask 200 will define where micro-needles, according to the present invention, are to be formed, and helps define locations and dimension for the micro-needles under fabrication.

Figure 1D:
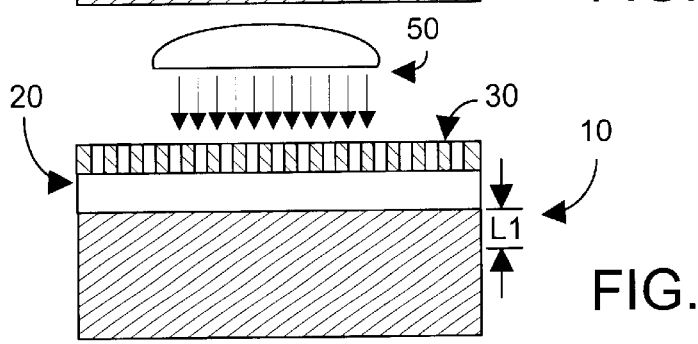
FIG. 1D depicts the wafer of FIG. 1C subjected to deep reactive ion etching, showing location of seeds if an alternative procedure is practiced, according to the present invention.

FIG. 1D depicts photoresist 30 and insulation layer 20 used as a mask for a deep reactive ion (RIE) etch 50. It is understood that thickness of the photoresist 30 will have been selected, as appropriate, to withstand RIE etch step 50. The etching step depicted in FIG. 1D forms the inverse of the desired micro-needles in the bulk of silicon wafer 10. The so-called Bosch dual-phase deep reactive ion etching process is used in the preferred embodiment, an etching process that involves alternating between silicon etching with an SF6 derived fluorine plasma and deposition of a passivating coating using a C4F8 derived polymer.

Figure 1E:
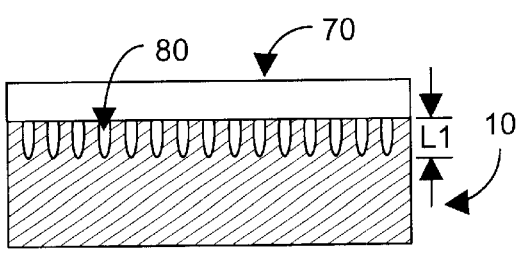
FIG. 1E depicts the wafer of FIG. 1D covered with a typically sacrificial layer of polysilicon, according to the present invention.

As shown in FIG. 1E, the etching process will form micro-needle like cavities in the silicon bulk. Etching process parameters such as the ratio between the duration of the etch portion of a cycle and the passivation portion can be varied to keep the side walls of the micro-needle cavities being formed vertical, or to form cavities that taper to a point within the silicon bulk. For example, cavity tapering may be achieved by increasing the passivation portion relative to the etching portion of a cycle.

The depth L1 into wafer 10 resulting from the etching process will be to a dimension at least as great as the desired length of the micro-needles under fabrication, when fabrication is complete.

As an alternative to RIE, a porous or macro-porous silicon etch step might be used. Details regarding use of such photo-assisted electrochemical etches may be found in V. Lehmann, J. Electrochem. Soc., Vol. 140, No. 10, October 1993, page 2836. Such electrochemical wet etching can be less expensive than plasma etching, and in many instances can produce holes and/or needles with smaller dimensions and/or greater aspect ratios.

If a porous or macro-porous Si etch step is used, at the pattern step depicted in FIG. 1C, a set of "seed" holes 60 would be etched in the Si prior to using the resist and insulator as an etch mask, as shown in FIG. 1D. Such seeds are shown in phantom in FIG. 1C. The required etch may be a short KOH etch or isotropic plasma etch to produce pits or holes of perhaps 1 µm depth.

Optionally as shown in FIG. 1E, a layer 70 of polysilicon or the like, perhaps 5 µm to perhaps 10 µm thick, may optionally be deposited into the newly etched needle-holes 80. Material 70 would be sacrificial, to be removed during backside KOH/TMAH (tetra methyl ammonium hydroxide)/ EDP (ethylene diamine pyrocatechol) etch, but can contribute substantially to the final height/diameter aspect ratio of the micro-needles to be formed. In a preferred embodiment, the profile of the micro-needles being formed is substantially vertical except near the needle tip.

Sacrificial layer 70 may be formed with low-pressure chemical vapor deposition, using thermal decomposition of silane at around 620° C. in a standard commercial furnace. If desired, a 1 µm thick layer of thermal oxide may be grown as a test wafer, e.g., in an atmospheric furnace in the presence of steam at 1100° C.

As an optional step, a deposition of Si3N4 to a thickness of perhaps 3,000 Å may be carried out, for example using LPCVD with dichlorosilane reacting with ammonia at around 750° C. Next a deposition of polysilicon may be formed, to a depth of perhaps 500 Å or so, followed by a deposition of tungsten to a thickness of perhaps 3,000 Å to about 5,000 Å, preferably carried out at about 285° C. at low pressure using WF6 (tungsten hexafluoride) and H2 gases. Of course other temperatures and deposition and/or etch regimes and/or dimensions may be used.

At this juncture, the micro-needle-like holes may be filed with polysilicon that may or may not be doped. This step may be performed with low-pressure chemical vapor deposition using thermal decomposition of silane at around 620° C. in a standard commercial furnace. If doping is desired, diborane or phosphine may be added to the furnace. Next, the outer layers of polysilicon and tungsten are removed from the wafer upper surface (in this example), using etching carried out with a low-pressure fluorine-based plasma.

During processing, oxides, nitrides, polysilicon, LPCVD and such usually deposit on both surfaces of wafer 10. Accordingly, all layers are now preferably etched from the bottom surface of wafer 10. This etch removal preferably is carried out in a low-pressure fluorine-based plasma for tungsten and polysilicon material, followed by wet etching in a bath of buffered oxide etchant to remove oxide material. A deposition of perhaps 1 µm thick conductive material, e.g., aluminum with 1% silicon, is made, preferably using a sputter deposition carried out with commercially available argon sputter equipment.

Figure 1F:
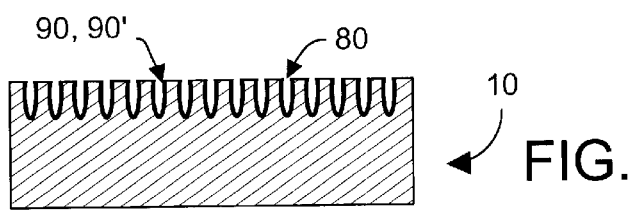
FIG. 1F depicts the wafer of FIG. 1E coated with a layer of thermal oxide or silicon nitride, according to the present invention.

Assume, on the other hand, that layer 70 has not been formed. At this juncture, as shown by FIG. 1F, a growth and/or deposition of thermal oxide 90 or a silicon nitride layer 90' is made to coat the inner surface of the newly etched needle-holes 80. It is understood that although the figures are shown two-dimensionally, a three-dimensional array of needle-holes will be thus etched.

Figure 1G:
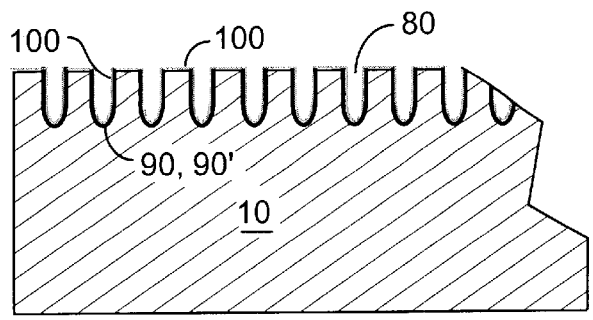
FIG. 1G depicts an enlarged portion of the wafer of FIG. 1F covered with a deposition of polycrystalline silicon, according to the present invention.

Referring to FIG. 1G, preferably using LPCVD, a thin layer of polycrystalline silicon 100 is deposited atop wafer 10 and on the inner surface of the needle-holes 80.

Figure 1H:
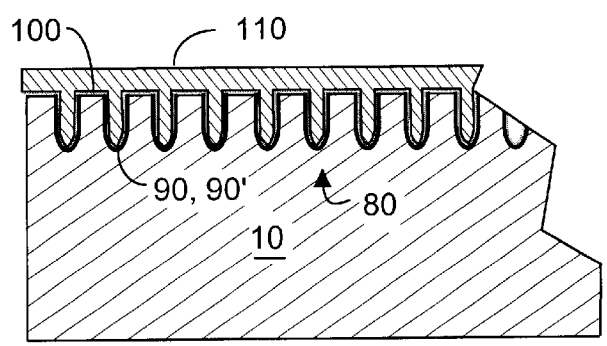
FIG. 1H depicts the wafer portion of FIG. 1G with a deposition of tungsten, according to the present invention.

Referring to FIG. 1H, if solid needles are to be formed, tungsten 110 is now deposited onto polysilicon layer 100, and may fill the needle-holes 80. If the needles to be produced will be hollow, this tungsten deposition step may be omitted.

Figure 1I:
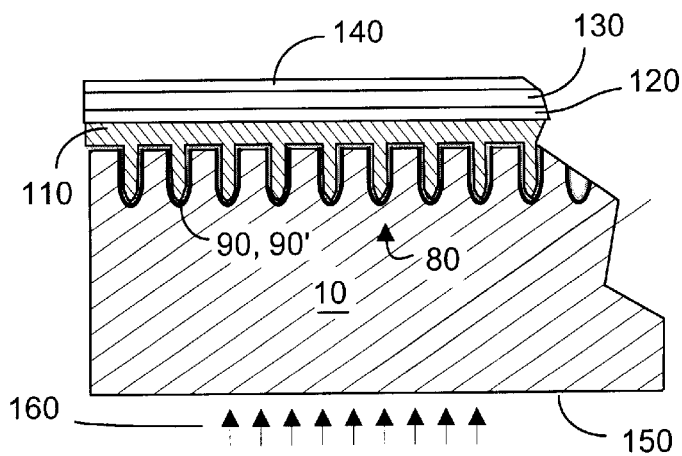
FIG. 1I depicts the wafer portion of FIG. 1H after deposition of a low temperature oxide layer, nitride layer, and polysilicon or epitaxial silicon layer, according to the present invention.

FIG. 1I depicts the structure after the upper surface of wafer 10 and the exposed surface of needle-holes 80 has been protected by depositing a low temperature oxide 120, depositing Micro-195-W wax, depositing a silicon nitride layer 130, and depositing and oxidizing a layer of polysilicon (or epitaxial silicon) 140. Silicon 140 could be used to completely fill the needle-holes where solid needles are to be fabricated.

Figure 1J:
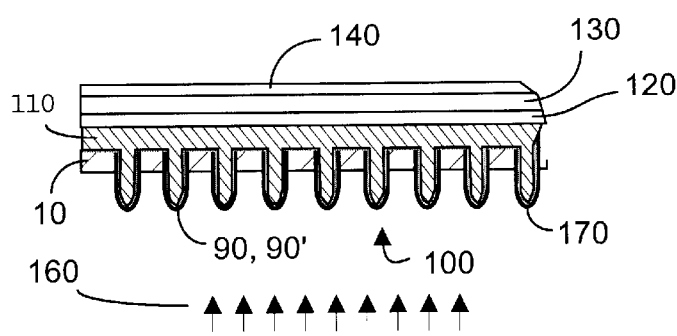
FIG. 1J depicts the wafer portion of FIG. 1H after the backside silicon structure has been removed to expose at least the distal tips of the micro-needles thus formed, according to the present invention.

Referring to FIGS. 1I and 1J, the bottom surface 150 of wafer 10 is now patterned using standard photolithography and a plasma etch or a wet etch (collectively, 160) to remove the various deposited and/or grown layers. Preferably a wet KOH or TMAH (tetra methyl ammonium hydroxide) or xenon difluoride, or other silicon enchant is used, an enchant that selectively etches silicon more than silicon oxides or nitrides.

As shown in FIG. 1J, such etching occurs on the backside of the wafer until at least part of the tips 170 of the micro-needles 160 are exposed. In FIG. 1J, etching has exposed approximately half the length of the underlying micro-needle structure.

Figure 1K:
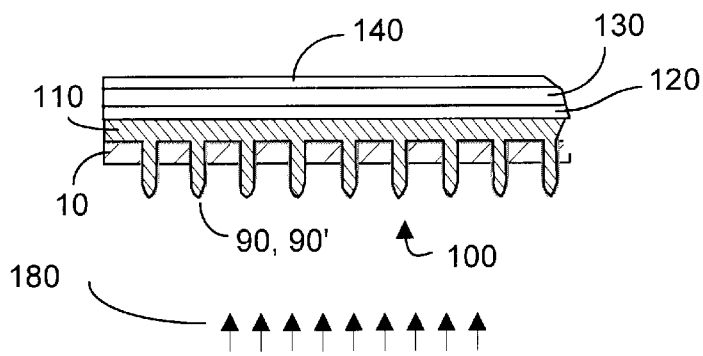
FIG. 1K depicts the wafer portion of FIG. 1J after further etching to expose a desired length of micro-needles thus formed, according to the present invention.

Referring to FIG. 1K, the exposed micro-needle tips 170 are subjected to a wet or a plasma etch 180 to remove at least a partial thickness of the insulating protective covering layer of silicon oxide or nitride 90, 90'. The wet silicon etch (e.g., KOH) is continued until a desired vertical height L2 of needle protrudes above the single crystal silicon membrane 110 on the topside of what was wafer 10.

Figure 1L:
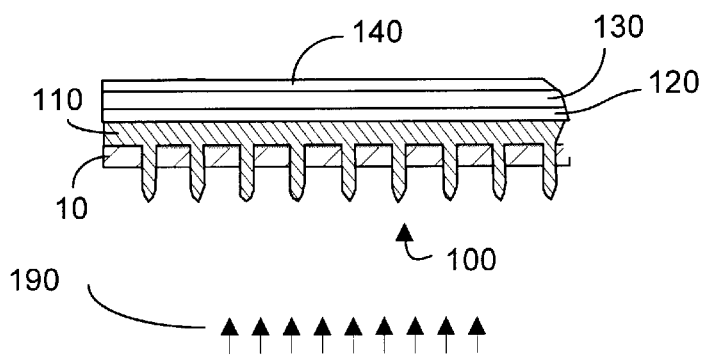
FIG. 1L depicts the wafer portion of FIG. 1K after a further wet etch to completely expose the tips of the micro-needles thus formed, in which hollow and solid formed needles are depicted, according to the present invention.

Referring to FIG. 1L, a second wet etch 190 is used to remove the remaining insulating material covering the needle tip. Depending upon whether the needle was hollow or solid in cross-section, the result at this juncture is a metallic micro-needle probe point or an opening in a long protruding capillary micro-needle. In FIG. 1L, by way of example, the right-most two micro-needles are shown as having been fabricated hollow.

It will be appreciated that the above process may be appended to a process used to fabricate transistors. For example, various steps of etching, lining, and filling the needle-holes could be incorporated partway through a CMOS fabrication process, for example at the same stage as a selective deposition of tungsten occurs in forming standard BiCMOS devices. Conductive traces may be patterned on the upper surface of the wafer before or after the holes are etched in the wafer. If desired, any additional peripheral holes may be etched and used as conductors to bring electrical signals to the lower portion of the wafer.

Assume that aluminum traces and wire bond pads are to be formed such that electrical signals may be conducted to individual ones of a plurality of conductive micro-needles, fabricated according to the present invention.

Figure 2B:
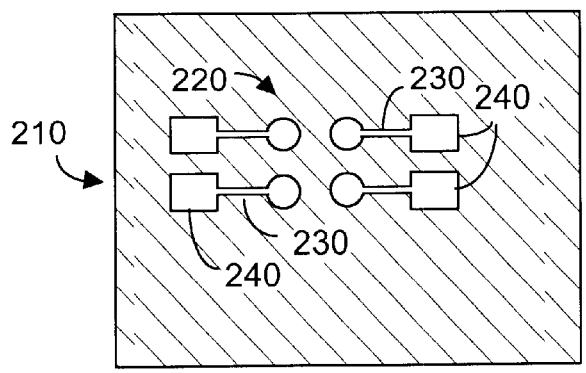

Referring to FIG. 2B, mask 210 is sized similarly to mask 200, and now defines a pattern 220 whose circular shaped regions align with what was pattern 40 in mask 200 (see FIG. 2A). However pattern 220 defines regions including trace regions 230 and wire bond pad regions 240. Ultimately these regions will be formed with aluminum or other electrically conductive material on wafer 10.

Figure 1M:
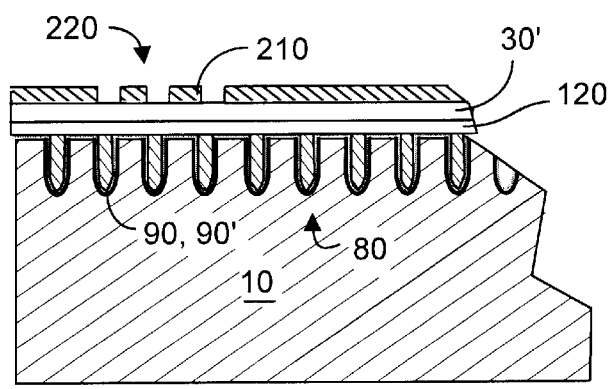
FIG. 1M depicts formation of bond traces and pads to couple electrical signal to individual micro-needles, formed according to the present invention.

Referring to FIG. 1M, preferably a layer 30' of standard photoresist such as Shipley S1813 or 3618 having a thickness of about 1 μm is spun onto the relevant surface of wafer 10, using a commercially available coater. Mast 210, as exemplified by FIG. 2B, overlies layer 30', and a standard mask aligner is used to expose underlying photoresist 30'. Development of the exposed photoresist is carried out according to the directions provided by the manufacturer of the resist.

Figure 1N:
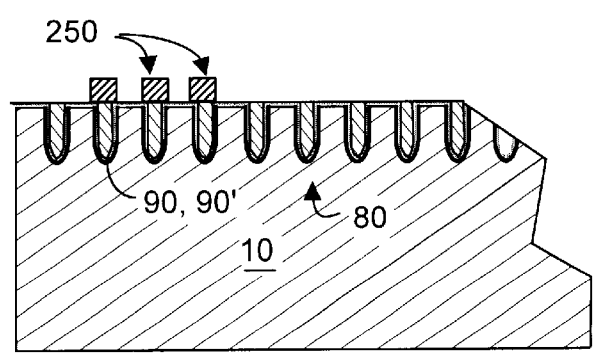
FIG. 1N depicts formed bond traces and pads in electrical connection with underlying micro-needles, according to the present invention.

Next, the exposed regions of wafer 10 are etched, using a dry (plasma) process, or a wet etch, using a commercially available aluminum etchant. Annealing of the resultant structure at perhaps 450° C. is carried out to improve electrical contact between the deposited aluminum pad and trace regions and underlying electrically conductive polysilicon regions. FIG. 1N depicts a simplified structure as this juncture, with electrically conductive traces and pads indicated as 250. Conductive pads 250 are in good electrical connection with, in this example, underlying ones of electrically conductive micro-needles.

According to the present invention, an oxide layer is now deposited on the upper surface (in this example) of the structure shown in FIG. 1N. This deposition may be carried out using a low temperature oxide (LTO), preferable with an LPCVD furnace using the reaction of oxygen and silane at around 400° C.

Figure 2C:
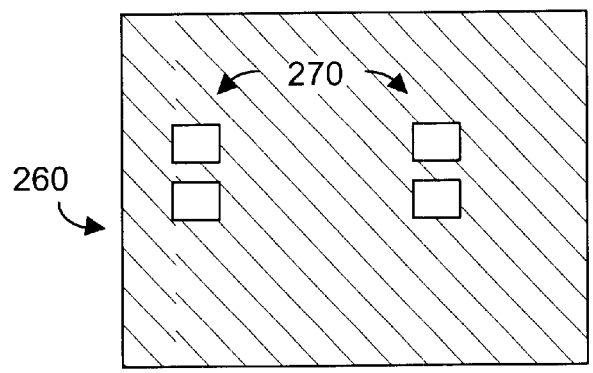

Referring now to FIG. 2C, mask 260 defining pattern 270 is used to etch windows in the above-described oxide layer that was deposited over wire bond pads and traces 250. A standard photoresist such as Shipley S1813 or 3618 may be used, with a resist thickness of around 1 μm, spun on to the underlying structure using a commercial coater. A standard mask aligner is used to expose the photoresist via pattern 270. Resist development is carried out according to directions from the resist manufacturer.

A pad etching step is carried out to expose the underlying wire pads 250. A deposition of low temperature oxide deposited to a thickness of perhaps 5,000 Å is carried out, preferably with a LPCVD furnace that uses the reaction of oxygen and silane at around 400° C. This step advantageously will protect the upper surface of the present structure from a TMAH etch, described below.

Figure 2D:
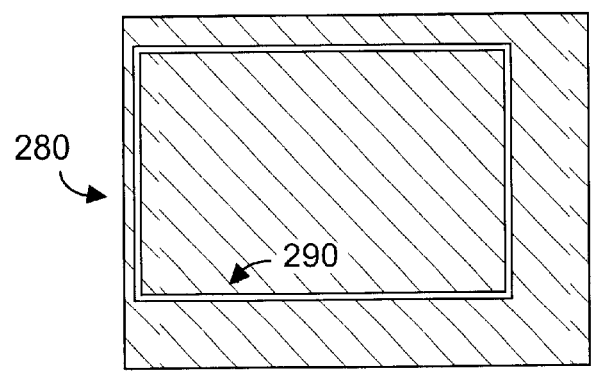

Referring now to exemplary mask 280 as shown in FIG. 2D, a scribe pattern 290 is defined in the mask to clear scribe lanes between micro-needle array dice. This definition is carried out with etching, for example TMAH (tetra methyl ammonium hydroxide) or a SF6 based silicon-etching plasma. A standard photoresist such as Shipley S1813 or 3618 is used with a thickness of around 1 μm, spun on using a commercial coater. A standard mask aligner is used to expose the photoresist, which is developed per resist manufacturer. Next, the low temperature oxide (LTO) is stripped away from the lower surface of wafer 10, and oxides are cleared from the scribe lanes defined on the upper surface of the wafer, by pattern 290 in mask 280.

The upper surface of wafer 10 may now be spun-coated with standard photoresist followed by a wet etch in buffered oxide etch, preferably containing hydrofluoric acid. An etch such as TMAH is now employed to uncover perhaps 5 μm lengths of the tip regions of the micro-needles formed according to the present invention.

A 20% tetra methyl ammonium hydroxide (TMAH) aqueous solution at between 50 C and 95 C to etching the expose silicon on the back side and the scribe lanes on the top side. Etching may be continued until the distal pointed tips of the formed micro-needles are visible, as seen with a microscope. The exposed oxide coating on the micro-needle tips are subjected to a HF vapor etch, e.g., using a dilute 20 percent HF aqueous solution to etch away about 50% of the oxide coating thickness. The TMAH etch may be continued to remove perhaps an additional 200 μm of material, until a desired height of micro-needles is exposed.

A P-etch may be carried out expose wire pads 250. A brief etching of uppermost surface of wafer 10 will remove the LTO covering on the aluminum wire bond pads. This LTO removal may be carried out using a dilute HF vapor or using a commercial pad etchant bath. An HF vapor etch may be carried out on the lower surface of wafer 10 to remove remaining oxide coating from the tips of the exposed micro-needles.

In the various procedures described herein, it is not required that the size of the various micro-needles produced in an array be identical. Multiple hole diameters may be used to provide an array with micro-needles having the same or different heights. Further, multiple micro-needle etching and fill steps may be iterated to produce micro-needles having various profile characteristics, e.g., inwardly tapering, outwardly tapering, no taper (cylindrical), hourglass shaped, etc.

Etching may be varied partway through the process of a micro-needle/hole to modify the profile as a function of depth. For example, an etch recipe for a high-aspect vertical walls could be used to etch a deep set of holes, whereafter the etch recipe could be modified such that as further etching occurs, the bottom of the hole would come to a point rather than being flat.

Referring now to FIGS. 1O–1U, a preferred method of forming arrays of open-ended hollow micro-needles will now be described. In FIG. 1O, a preferably SEMI single-sided single crystal silicon wafer 10 will have had at least its upper surface polished. A resist (not shown) is spun-on the polished upper wafer surface, and is patterned, using conventional photolithographic techniques. Although not shown in FIG. 1O, the thus patterned wafer is etched, for example using an SF6 based plasma etch, to define a fluidic channel or reservoir 115. The resist is removed from the upper surface of wafer 10, and a deposition of silicon nitride (SiN) 90' is made to the lower wafer surface, preferably using LPCVC with ammonia and silane.

Referring now to FIG. 1P, a preferably thick (e.g., perhaps 5 μm to 15 μm) layer of resist 30 such as AZ4620 photoresist is spun onto the upper surface of wafer 10 and patterned using standard lithography to define openings 35 where hollow micro-needle cavities are to be formed in the bulk of wafer 10.

As shown in FIG. 1Q, a deep RIE (DRIE) etch step is carried out until cavity holes 45 are formed, extending entirely through wafer 10, e.g., from the upper wafer surface down to SiN layer 90' on the lower surface. A Bosch type DRIE etch process is preferred for this step although in some applications a photo-assisted electrochemical etch may be used.

FIG. 1R shows wafer 10 following the etching process, and depicts fluidic channels or reservoirs 115 and cavities 45 in which hollow micro-needles will be formed. As noted earlier it is not required that each cavity 45 be similarly sized, and in FIGS. 1Q and 1R the right-most cavity is shown having a smaller cross-section than the left-most cavity. For ease of illustration both cavities have been depicted with cylindrical sidewalls. However as noted earlier, cavity configuration (which is to say mold configuration or ultimately micro-needle configuration) can exhibit various desired profiles, including cylindrical, tapering, tapering-out, hourglass, etc.

Referring now to FIG. 1S, a layer of thermal silicon dioxide 125 is grown on the exposed surfaces of wafer 10, typically layer 125 will have a layer thickness of perhaps 1 $\mu$m to perhaps 3 $\mu$m. Those skilled in the art will appreciate that no silicon dioxide will deposit upon SiN layer 90'. Referring now to the lower portion of FIG. 1S, in the next processing step, SiN layer 90' is removed with etch 50", preferably a plasma or wet etch.

Figure 1T:
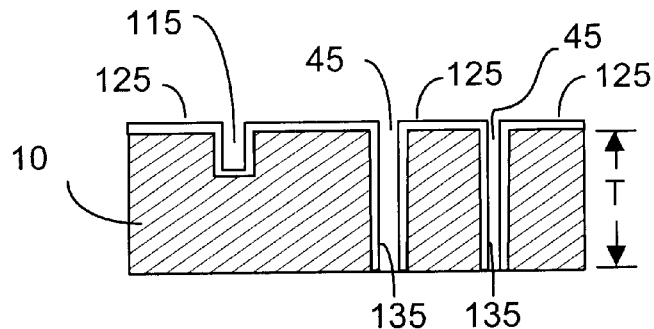
FIG. 1T depicts the wafer of FIG. 1R after removal of the SiN layer, the resultant structure having channel or reservoir depressions on the upper wafer surface, and hollow micro-needles extending from the lower wafer surface, according to the present invention.
Figure 1U:
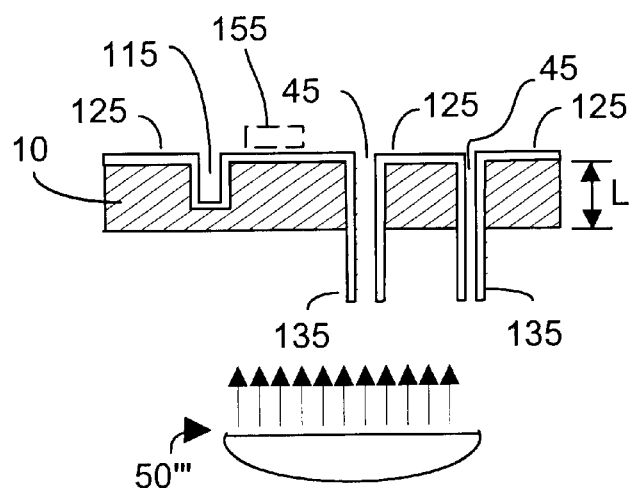
FIG. 1U depicts the wafer of FIG. 1R after the backside silicon structure has been removed to expose a desired length of the hollow micro-needles protruding from the lower wafer surface, according to the present invention.

At this juncture, the structure is as shown in FIG. 1T. The length T of hollow micro-needles 135 (see FIG. 1U) is essentially buried within the bulk of substrate 10. But as shown in FIG. 1U, a preferably TMAH etch process 50'" is carried out to remove a fractional thickness of the bulk of wafer 10, starting from the bottom wafer surface. In this fashion, the exposed length of hollow micro-needles 135 will have a dimension (T-L), which dimension can be controlled by etch process 50'".

The resultant structure, as shown in FIG. 1U, exhibits fluidic channels or reservoirs 115, and hollow micro-needles 135, fabricated in this example from silicon dioxide. The silicon dioxide could be replaced with other material, and if desired, all or part of the hollow micro-needles 135 might be made electrically conductive, for example by deposition of conductive material.

Shown generically in the structure of FIG. 1U is element 155, which represents other structure(s) that may be fabricated upon or physically attached to wafer 10. Structure 155 might include a separate wafer that is bonded or otherwise physically attached to wafer 10, which separate wafer may include electronics and/or mechanical and/or thermal devices useful with the structure(s) formed on wafer 10. Alternatively, structure 155 might represent electronics and/or mechanical and/or thermal devices fabricated on wafer 10. By way of example, it might be useful to provide micro-pumps and/or micro-diaphragms and/or micro-paddle wheels on or adjacent wafer 10, for use in a fluidic application. It might be useful to provide electronics on or adjacent wafer 10, perhaps to control electronic signals coupled to chosen ones of micro-needles. In a hollow micro-needle application, for example, various of the hollow micro-needles might be made conductive, and subjected to electronic signals governed by electronics 155, perhaps to control a micro-array of fluid jets, or the like.

Referring once more to FIG. 1Q, if desired etch process 50' could be carried out to etch entirely through wafer 10. In some process procedures where DRIE etching is to be used, it can be advantageous to bond micro-needle wafer 10 to a carrier wafer, for example using a thin layer of photoresist. Alternatively, micro-needle wafer 10 could simply have a coating of oxide on its back side. Either procedure can advantageously prevent pressurized helium used as coolant in some DRIE systems from leaking through the openings 45 etched in micro-needle wafer 10.

In the preferred implementation, this is carried out using an n-type silicon wafer. Diameter of the micro-needles that are ultimately formed will be inversely dependent upon net doping concentration of the silicon wafer. A net donor concentration of a few times $10^{-12}$ will form micro-needles with diameters of around 10 $\mu$m. Higher doping concentrations would result in narrower diameter micro-needles. The diameter of holes etched with this process may also be controlled by varying the supply of electronic holes generated by back side illumination. This basic porous silicon etching process is known to those skilled in the art, and may be found in many treatises and papers, including V. Lehmann, "The Physics of Macroporous Silicon Formation," Thin Solid Films, 255 (1995)1–4. and H. Ohji, P. T. J. Gennissen, P. J. French, and K. Tsutsumi, "Fabrication of a Beam-Mass Structure Using Single-step Electrochemical Etching for Micro Structures (SEEMS)," J. Micromech. Microeng. 10 (2000) 440–444.

If desired, the earlier-described DRIE etching step to form through-wafer holes may be replaced with a porous-silicon, electrochemical etch. In the earlier step of etching off silicon nitride, silicon nitride could be deposited as a masking material, in which case no thick resist would be needed. Instead, a standard resist would suffice to pattern the silicon nitride layer using a sulfur-hexafluoride and Freon based plasma etch. The silicon nitride would be best deposited via LPCVD involving silane and ammonia. Between the earlier-described steps of spinning on thick resist and performing DRIE to form through-wafer holes, a short KOH anisotropic etch would be used to form sharply pointed pits where the silicon nitride was removed. These KOH pits will then form 'seed' holes for the micro-needles, as described elsewhere earlier herein.

Etching preferably would occur in a bath of aqueous hydrofluoric acid with a concentration of between about 2% to about 6% HF. The wafer would be kept in the dark, except that the backside of the wafer would be illuminated with light with wavelengths shorter than around 700 nanometers. Such light would generate electronic 'holes' that would diffuse to the points of the KOH seed pits. In N-type silicon, the reaction of the silicon with the hydrofluoric acid requires these photo-generated electronic 'holes' to proceed.

Figure 3A:
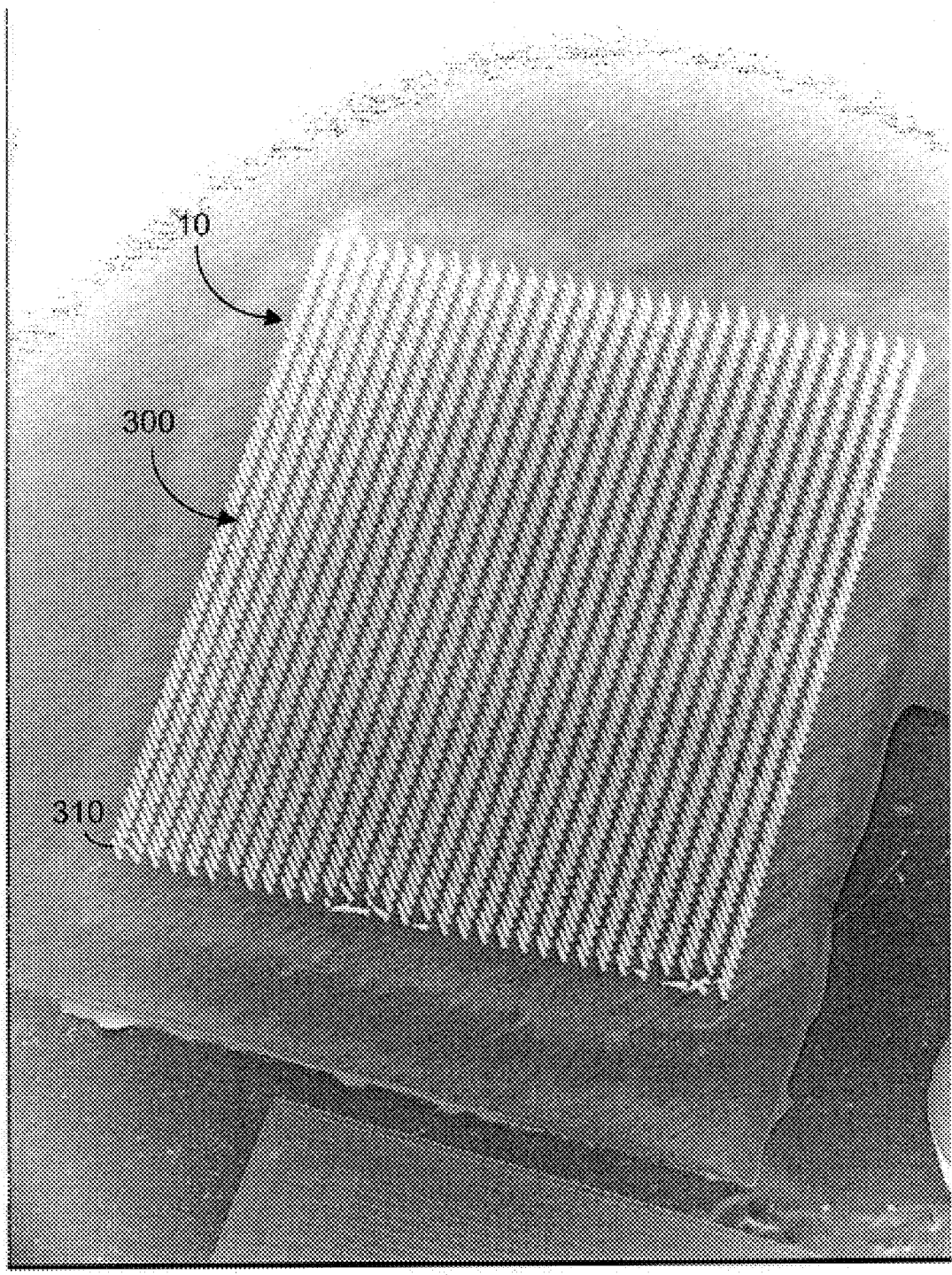
FIG. 3A in an image of an array of micro-needles, fabricated according to the present invention.
Figure 3B:
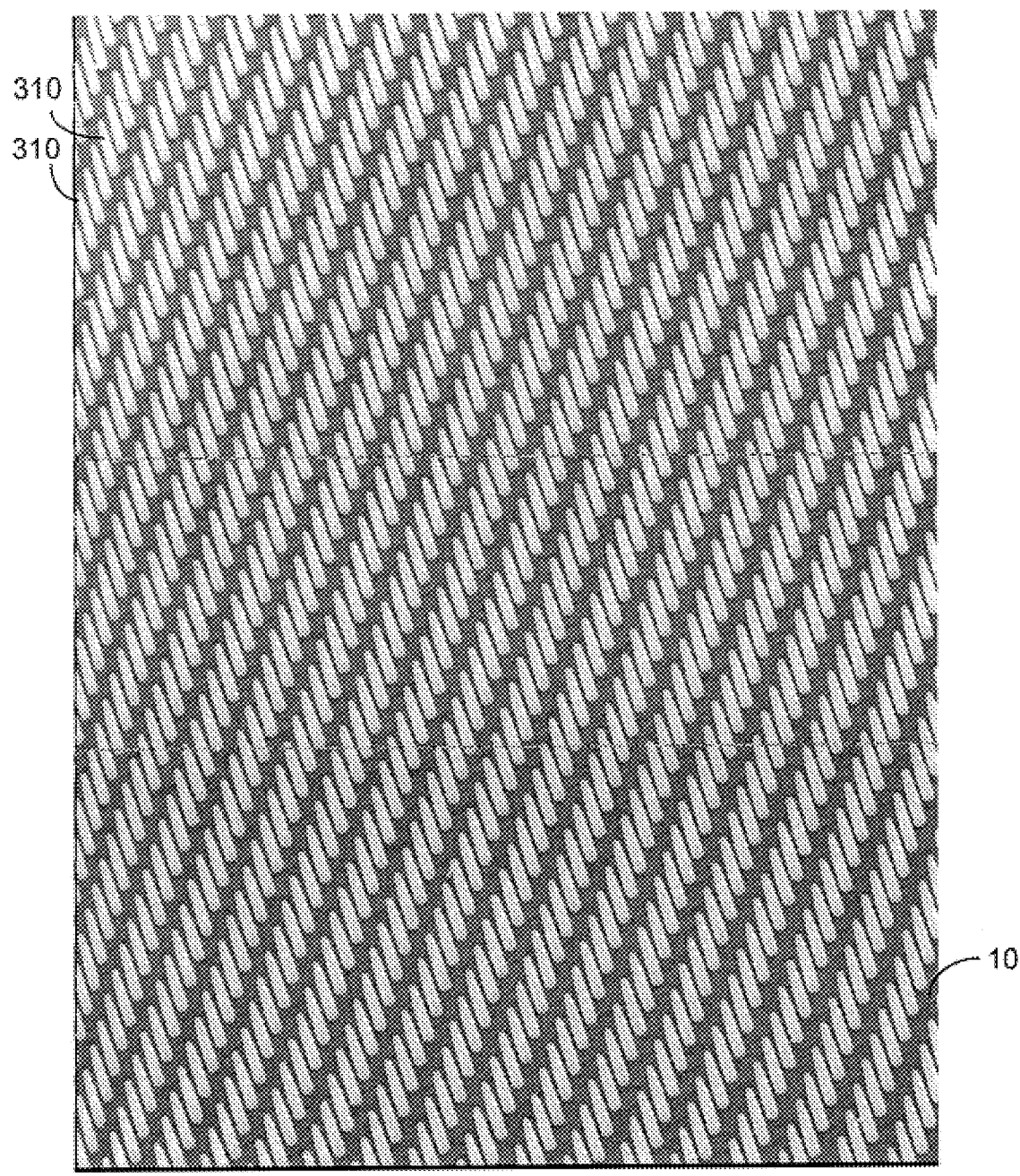
FIG. 3B is a close-up of a portion of the array of FIG. 3A.

FIG. 3A depicts a 32 column by 64 row array 300 of micro-needles 310 fabricated according to the present invention. The micro-needles shown were formed on a pitch of 100 $\mu$m by 50 $\mu$m, upon an underlying substrate 10 of single crystal silicon. Micro-needles 310 were formed following the procedure described herein for fabricating hollow micro-needles, except that the etch step to open the distal tips of the micro-needles has not been carried out in FIG. 3A. FIG. 3B is a close-up showing individual micro-needles 310 in the array of FIG. 3A.

Figure 3C:
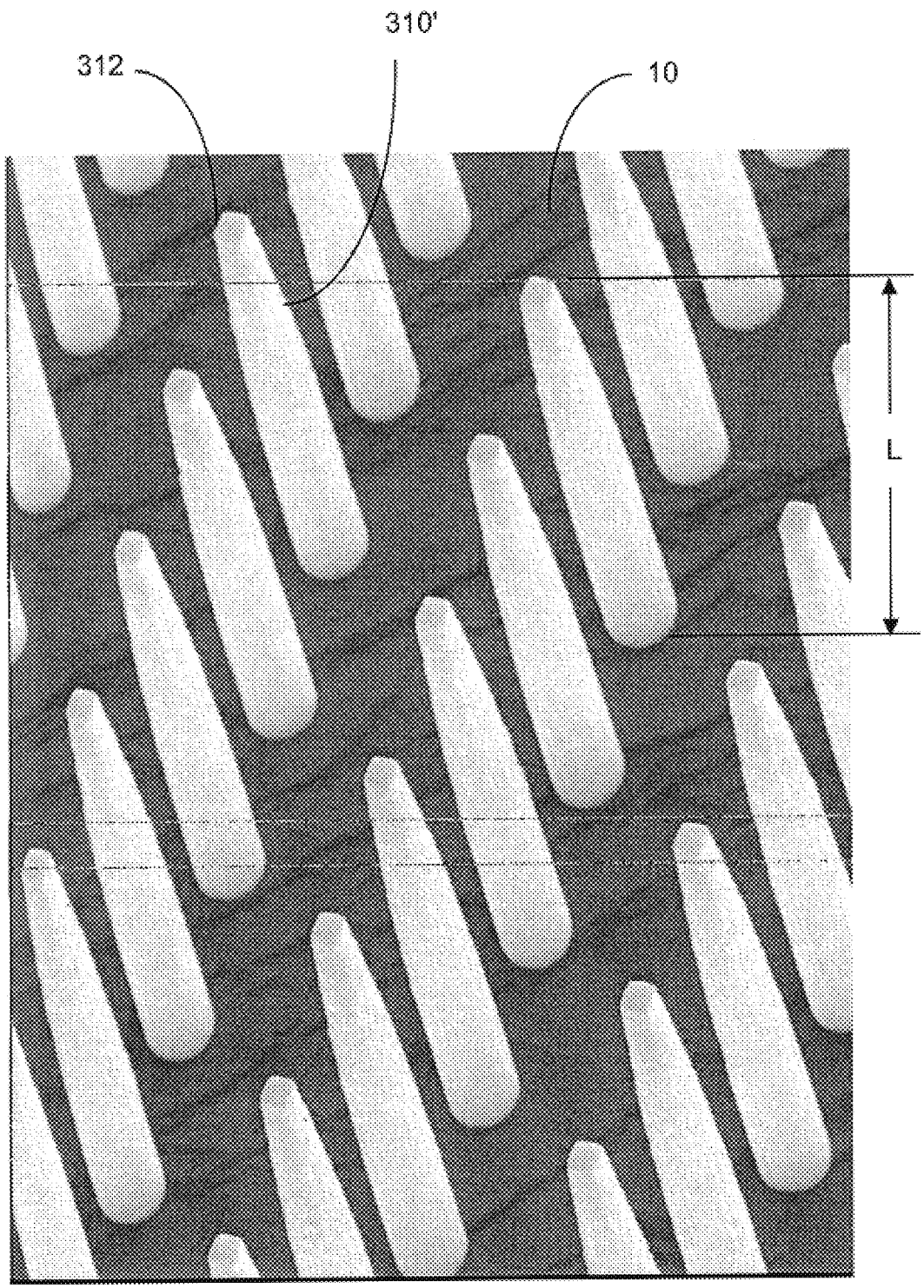
FIG. 3C is a close-up of a portion of an array of flat-topped hollow glass micro-needles, fabricated according to the present invention.

FIG. 3C is a close-up view of a portion of an array of hollow glass micro-needles 310', whose distal tips 312 are formed with a flat surface. The array pitch in FIG. 3C is 50 $\mu$m by 100 $\mu$m, and the exposed projecting height L of each micro-needle above the surface of wafer substrate 10 is about 110 $\mu$m.

Figure 3D:
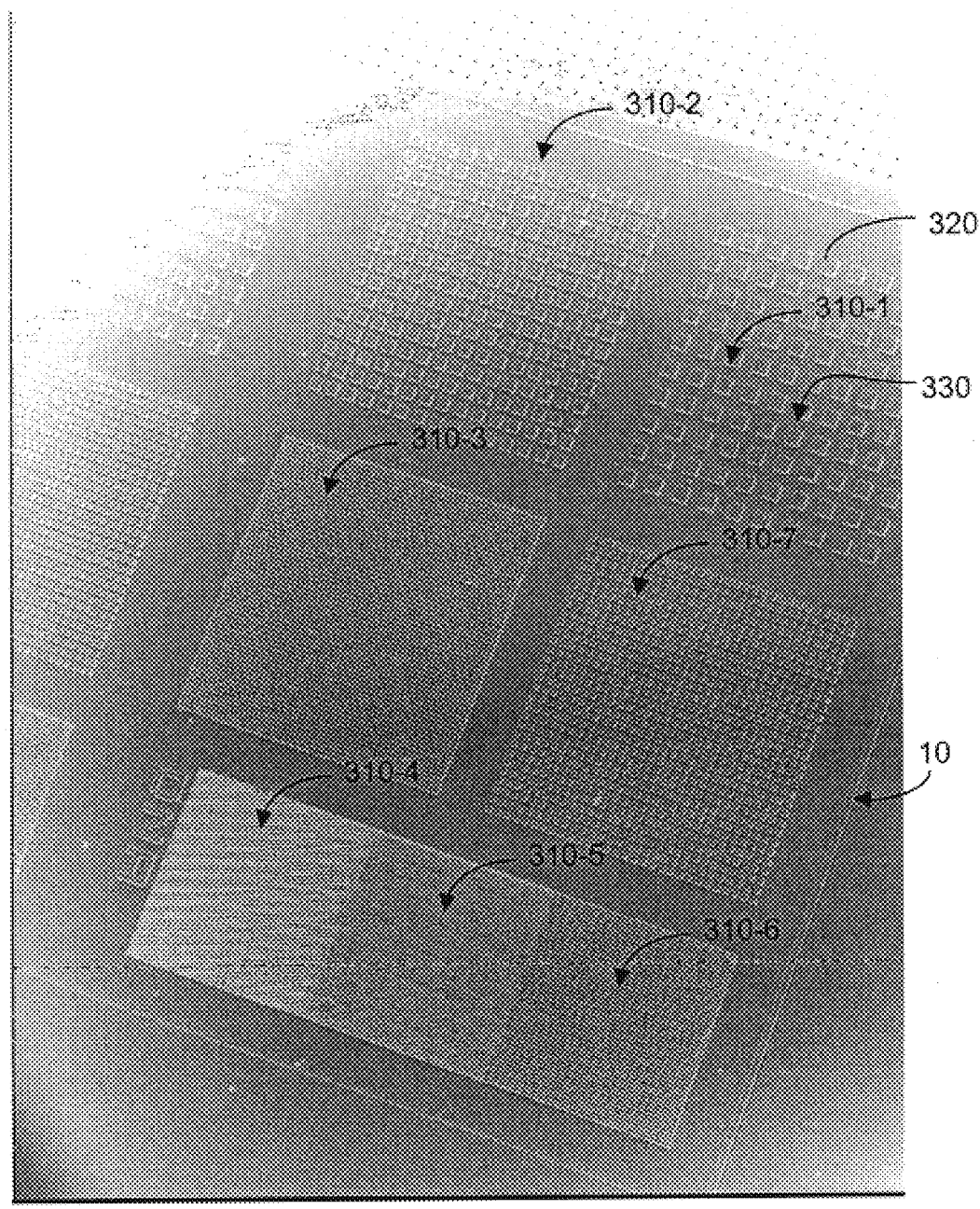
FIG. 3D is an image depicting several arrays of differently pitched micro-pillars that may be used as negative molds to form polymer well substrates, according to the present invention.

FIG. 3D is an image showing seven arrays 310-1, 310-2, . . . 310-7 of micro-pillars 320 that can act as a negative mold to fabricate inexpensive polymer well substrates. The pitch of array 310-1 is 80 $\mu$m by 150 $\mu$m, array 310-2 has a pitch of 60 $\mu$m by 100 $\mu$m, array 310-3 has pitch 30 $\mu$m by 50 $\mu$m, array 310-4 has pitch 15 $\mu$m by 25 $\mu$m, array 310-5 has pitch 10 $\mu$m by 20 $\mu$m, array 310-6 has pitch 6 $\mu$m by 10 $\mu$m, and array 310-7 has pitch 3 $\mu$m by 10 $\mu$m. In FIG. 3D, the vertical height of each raised negative well 320 above the planar surface of substrate 10 is about 20 $\mu$m. Substrate 10 is again single crystal silicon, which here is covered with a layer of PTFE-like polymer film 330. Film 330 substantially reduces the sticking coefficient between the polydimethyl siloxane (PDMS) and the mold used in forming PDMS well-chips. The resultant structure is suited for making so-called gene chips, as described elsewhere herein.

Figure 3E:
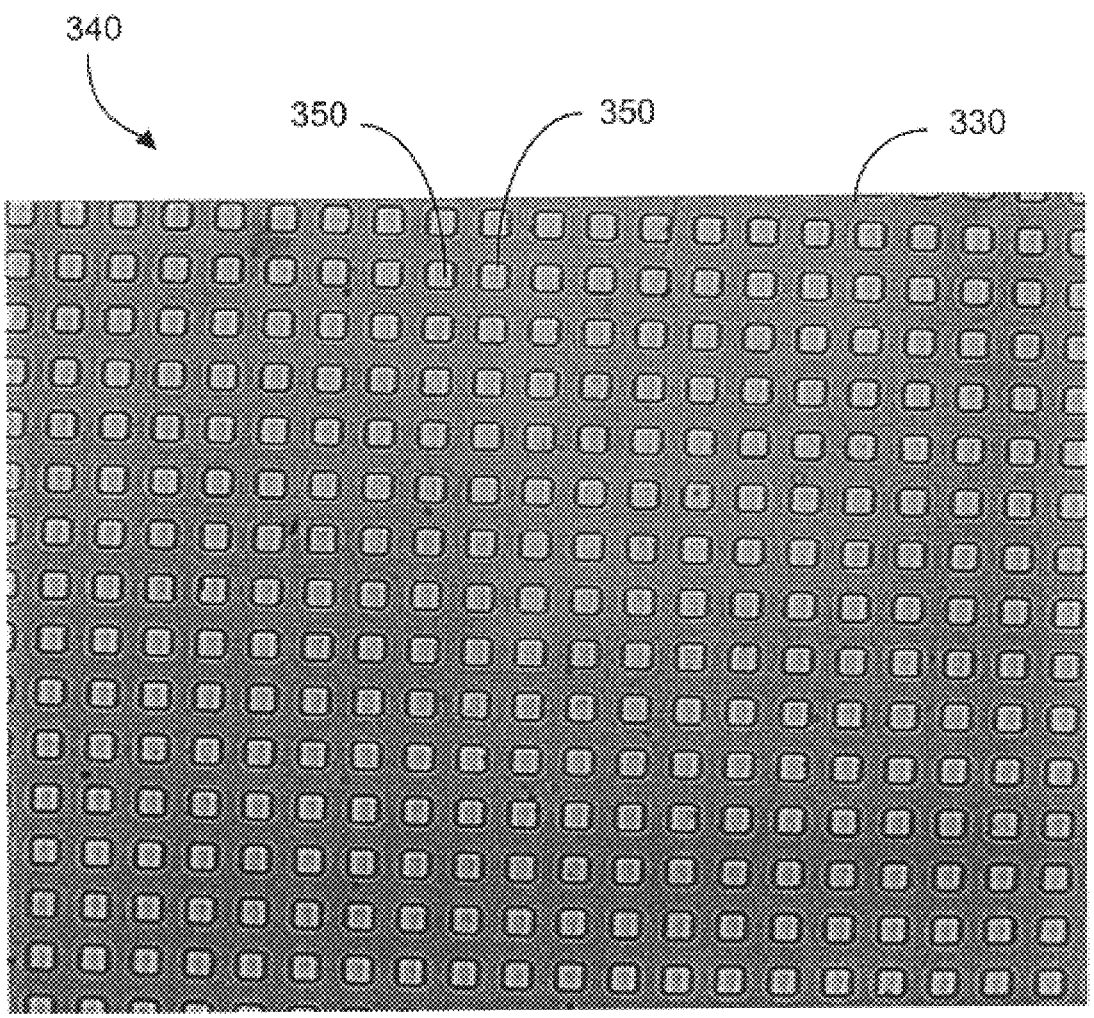
FIG. 3E depicts an array of wells formed on a polydimethyl siloxane (PDMS) substrate from the silicon mold depicted in FIG. 3D, according to the present invention.

FIG. 3E depicts an array 340 defined by a PDMS substrate 330 in which a plurality of wells 350 have been molded. Each well 350 is about 20 $\mu$m deep and about 20 $\mu$m wide, and array 340 has a well-to-well pitch of about 50 $\mu$m. Array 340 in FIG. 3E was in fact fabricated using the silicon mold depicted in FIG. 3D.

Figure 3F:
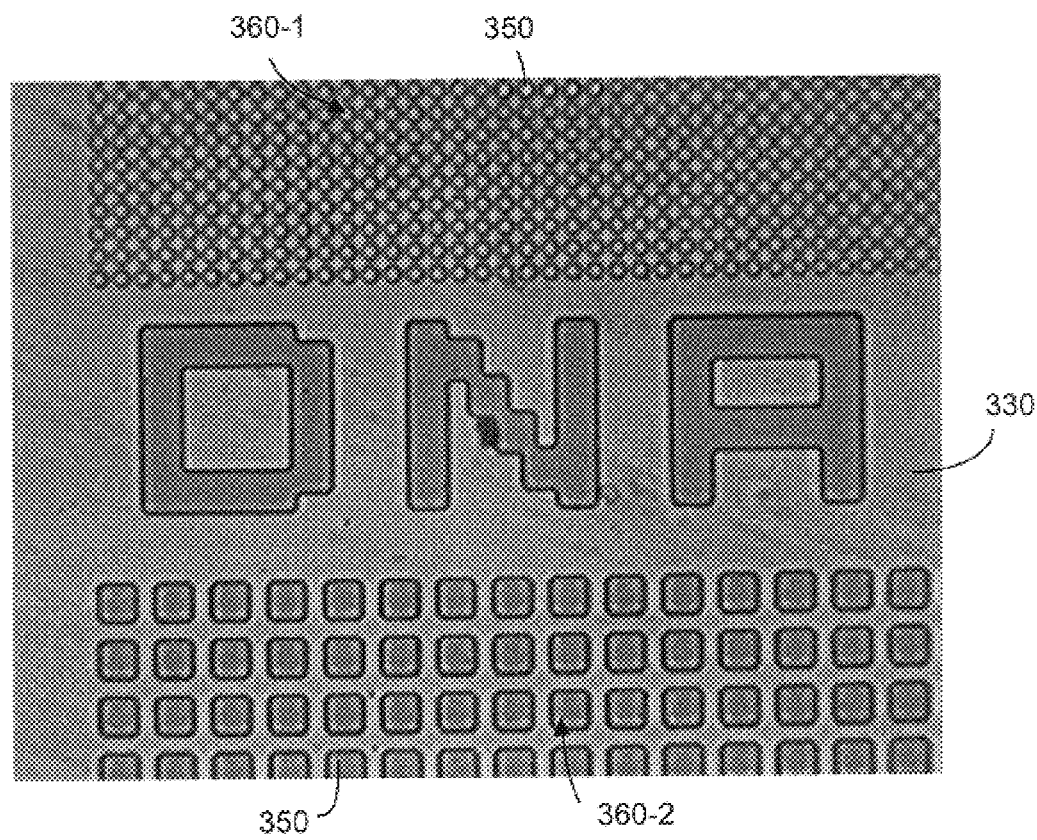
FIG. 3F depicts an elastomer PDMS substrate upon which are formed arrays having differently pitched PDMS pillars that may themselves be used as a mold for another polymer, according to the present invention.
Figure 3G:
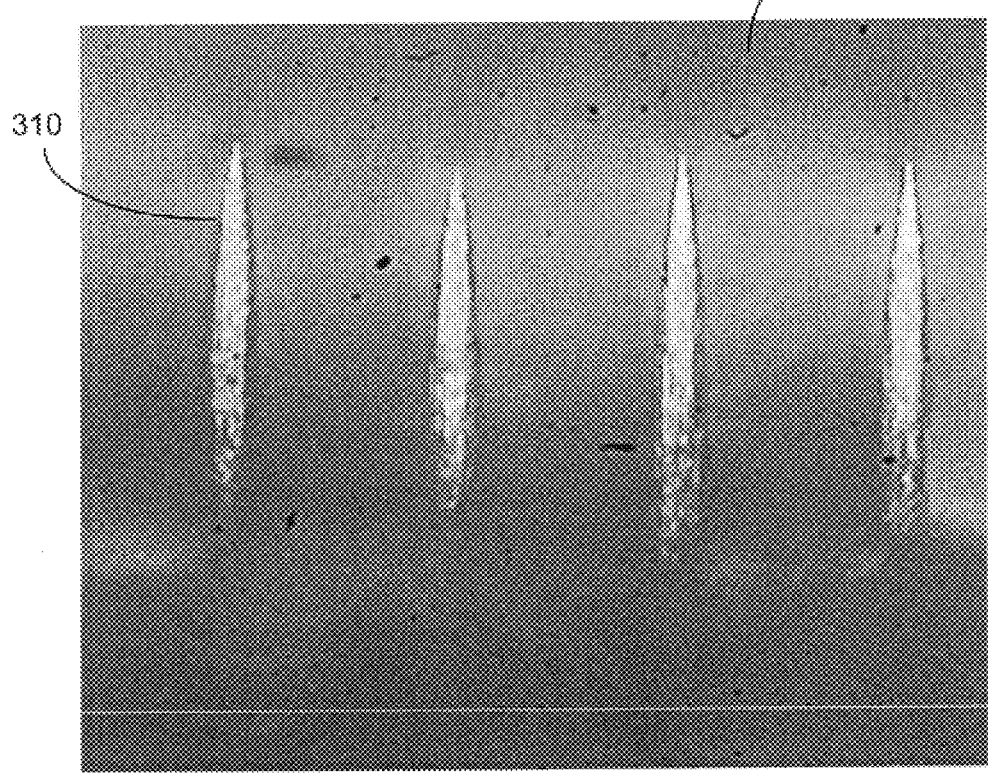
FIG. 3G is an image depicted tapered micro-needles, fabricated according to the present invention.

FIG. 3F depicts an elastomer PDMS substrate 330 upon which arrays 360-1 and 360-2 have been formed. Array 360-1 comprises a plurality of raised pillars 350 having 15 $\mu$m pitch and 10 $\mu$m pillar diameter, while array 360-2 comprises a plurality of raised pillars 350 having 50 $\mu$m pitch and 30 $\mu$m pillar diameter. PDMS pillars 350 were formed using a silicon substrate with wells defined therein to form a mold. Pillars 350 may themselves serve as an inexpensive mold for another polymer, polyurethane, for example. FIG. 3G is a close-up image showing micro-needles having a tapered profile, fabricated according to the present invention. In FIG. 3G, tapered micro-needles 310 have a conductive tungsten core, have a vertical height of about 110 $\mu$m, a base cross-sectional dimension of about 10 $\mu$m (in the structure shown, a diameter dimension), and have a pitch of about 50 $\mu$m.

Figure 4:
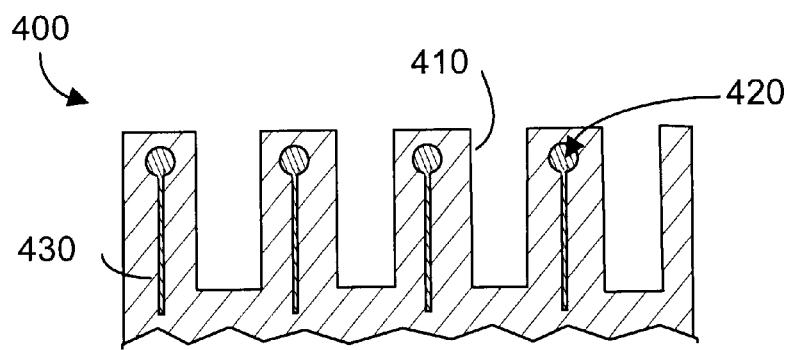
FIG. 4 depicts an array of flexible electrical micro-probes, according to the present invention.

Referring now to FIG. 4, a preferred method of forming flexible electrical probes arrays will be described. Arrays of micro-needles with conductive cores, such as have been described earlier herein, may be used to electrically probe devices, such as integrated circuits. Such probing is typically carried out in the prior art using a probe card constructed from a printed circuit board with an array of tungsten needles soldered to the circuit board. According to the present invention, an alternative method would use micro-needles, formed according to the present invention, but in which each micro-needle is formed at the end of a thin cantilever of single crystal silicon.

Fabricating such probes may be carried out using the above-described method for fabricating a bed of nails type array, with the addition of two steps. Between the steps of depositing polysilicon (if a thick micro-needle wall is desired), and depositing silicon dioxide to protect polysilicon within the micro-needle openings, a deep reactive ion etch (DRIE) step would be performed. The RIE etch may be masked by regular photoresist, and would be used to define the three sides of the cantilever. The silicon dioxide that was deposited to protect the polysilicon within the micro-needle holes will advantageously prevent further etching of these cantilever-defining trenches during a final wet silicon etch process to expose a desired micro-needle height. The step of carrying out an oxide etch will remove the protective oxide that hitherto defined the trenches. Thus, referring to the plan view of FIG. 4, a substrate structure 400 is shown in which trenches 410 have been defined to form micro-needles and preferably aluminum conductive traces (collectively 420, the circular portion being the plan view of a circular cross-section micro-needle) and a cantilever stalk 430. The bulk silicon in the region of the array preferably is etched down to a final thickness of 10 $\mu$m or less to ensure that the cantilever structures are sufficiently flexible, rather than being rigid.

For fluid applications of the completed array, channels and reservoirs may be etched into the upper wafer surface. Indeed, after the holes are filled and the upper surface planarized, membranes and/or pumps could be fabricated at the upper surface using standard MEMS techniques. More sophisticated structures can be implemented by disposing a structure on top of the needle-wafer structure, or on a second wafer bonded or otherwise joined to the needle-wafer structure. By way of example, the topside silicon surrounding each needle could be thinned and electrodes added. Another set of electrodes could be formed on a parallel surface, such that one could selectively and controllably move the membrane and thus move selected individual needles up and down vertically in the plane parallel to the longitudinal axis of the needle.

In certain biological applications, fluid may be dispensed onto a substrate or slide using a micro-needle fabricated according to the present invention. In such applications, an electrical potential may be coupled between the micro-needle and substrate or slide such that the dispensed fluid will prefer the substrate or slide rather than the needle.

In other applications, the present invention may be used to fabricate capillary needles for use in colloid micro-thruster arrays. Such arrays can be used in space propulsion among other uses. In such applications, a hole is formed through a substrate, through which hole a fluid droplet or jet is to be expelled. A potential is applied between the needle and substrate, the potential being sufficiently large to overcome the surface tension of the fluid. Typically the fluid will be glycerol or perhaps water doped with salt.

The present invention permits forming needle-like structures having diameters ranging from a micron or so up to at least hundreds of microns. The needle-like structure may be tapered with tip radii of less than 1 $\mu$m. Needle structure lengths may fabricated from perhaps 10 $\mu$m and up, to more than a millimeter. Needle pitches of 10 $\mu$m or so are readily achieved. If desired, the same sensor or wafer can include needles of different heights.

Fabrication materials may include, without limitation, silicon, aluminum, tungsten, glasses, silicon nitrides, silicon carbide, copper, most metals, Teflon-like polymers. Useable materials can probably include plastics, especially when the partially completed array is used as a mold and a completed array of metal needles is used to hollow-out a plastic needle array, using for example micro-embossing.

Modifications and variations may be made to the disclosed embodiments without departing from the subject and spirit of the invention as defined by the following claims.

What is claimed is:

1. A method of fabricating an array of micro-sized structures, comprising the following steps:

(a) polishing at least a first surface of a semiconductor wafer having said first surface and a spaced-apart second surface;

(b) patterning said first surface to define an array of open regions whereunder said micro-sized structures are to be formed;

(c) removing material from said wafer to a desired depth extending from said first surface toward said second surface in said regions defined at step (b);

wherein step (c) produces a mold structure defining an array of micro-sized cavities.

2. The method of claim 1, wherein said wafer is SEMI single crystal silicon.

3. The method of claim 1, where step (b) includes forming a pattern in which at least some of said open regions have a horizontal cross-section dimension ranging from about 1 nm to about 10 mm, and have a spaced-apart pitch ranging from about 1 $\mu$m to about 1 cm.

4. The method of claim 1, wherein step (b) includes defining at least one of said open regions with a cross-section pattern selected from a group consisting of (i)

circular, (ii) rectangular, (iii) triangular, (iv) line segment, (v) filled-in polygon, and (vi) hollow polygons.

5. The method of claim 1, wherein step (c) is carried out using an etch process.

6. The method of claim 1, wherein step (c) forms cavities in said wafer having a depth/cross-section dimension aspect ratio ranging from less than one to greater than one-thousand.

7. The method of claim 1, wherein step (c) is carried out to produce at least some said cavities having a vertical cross-section profile selected from a group consisting of (i) parallel vertical walls, (ii) vertical walls tapering inward, (iii) vertical walls tapering outward, and (iv) vertical walls defining a curve.

8. The method of claim 1, wherein step (c) forms said cavities with said desired depth ranging from about 1 μm to about 1 cm.

9. The method of claim 1, wherein at step (a) said wafer is n-type material, and at step (c) said etching includes an electrochemical etch.

10. The method of claim 1, wherein at step (c) said etching includes one of (i) deep reactive ion etching and (ii) porous silicon etching, and wherein at step (b) if deep reactive ion etching is employed at step (c) lithographic patterning substantially determines cross-sectional area of said cavities, and if porous silicon etching is employed at step (c) a vertical profile of said cavities is affected by intensity of light associated with said etching.

11. The method of claim 1, wherein step (c) includes etching with an electrochemical etch, and wherein cross-sectional area of said cavities is influenced by at least one factor selected from a group consisting of (i) any doping present in said substrate, (ii) light intensity associated with said etching, (iii) HF concentration of said etching.

12. The method of claim 1, further including:

(d) filling at least said cavities with a fill-material to form micro-needles of said fill-material; and (e) removing material from said wafer from said second surface toward said first surface to expose a desired length of said micro-needles;

wherein said fill-material is selected from a group consisting of (i) electrically conductive material, and (ii) electrically insulating material.

13. The method of claim 12, wherein said fill-material is formed with a hollow core such that said micro-needles are hollow.

14. The method of claim 12, wherein said fill-material includes polydimethyl siloxane (PDMS);

wherein removal of said PDMS from said mold produces a flexible array of cell micro-well regions useable in gene cell probing.

15. The method of claim 12, further including shaping at least a portion of said wafer such that at least one of said micro-needles projects from a cantilevered arm portion of said wafer.

16. The method of claim 12, further including forming on said first surface at least one of (i) a fluidic channel, and (ii) an electrically conductive trace.

* * * * *